(12) United States Patent
Consalvo et al.

(10) Patent No.: US 10,072,055 B2
(45) Date of Patent: Sep. 11, 2018

(54) ANTI-INFLAMMATORY PHARMACEUTICAL PRODUCTS

(71) Applicant: Resother Pharma APS, Holte (DK)

(72) Inventors: Angelo P. Consalvo, Monroe, NY (US); Nozer M. Mehta, Randoph, NJ (US); Mauro Perretti, London (GB); Jesmond Dalli, Brookline, MA (US)

(73) Assignee: Resother Pharma APS, Holte (DK)

( * ) Notice: Subject to any disclaimer, the term of this patent is extended or adjusted under 35 U.S.C. 154(b) by 62 days.

(21) Appl. No.: 14/803,426

(22) Filed: Jul. 20, 2015

(65) Prior Publication Data

US 2015/0315256 A1 Nov. 5, 2015

Related U.S. Application Data

(62) Division of application No. 13/524,381, filed on Jun. 15, 2012, now Pat. No. 9,102,753.

(60) Provisional application No. 61/497,270, filed on Jun. 15, 2011.

(51) Int. Cl.
*C07K 14/47* (2006.01)
*A61K 38/17* (2006.01)
*A61K 38/00* (2006.01)

(52) U.S. Cl.
CPC ...... *C07K 14/4703* (2013.01); *A61K 38/1709* (2013.01); *C07K 14/4721* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 9,102,753 | B2 * | 8/2015 | Consalvo | A61K 38/1709 |
| 2009/0163578 | A1 * | 6/2009 | Dorovkov | C07K 14/705 514/456 |
| 2012/0004175 | A1 | 1/2012 | Zhang et al. | |
| 2012/0270790 | A1 * | 10/2012 | Podgoreanu | A61K 38/1709 514/15.1 |
| 2013/0072446 | A1 | 3/2013 | Consalvo et al. | |
| 2015/0315256 | A1 * | 11/2015 | Consalvo | A61K 38/1709 514/21.3 |

FOREIGN PATENT DOCUMENTS

| | | | |
|---|---|---|---|
| WO | 2006/039621 | | 4/2006 |
| WO | WO 2006039621 | * | 4/2006 |
| WO | 2007/019376 | | 2/2007 |
| WO | 2007/022774 | | 3/2007 |
| WO | 2008/121881 | | 10/2008 |
| WO | 2009/081151 | | 7/2009 |
| WO | 2010/043045 | | 4/2010 |

OTHER PUBLICATIONS

Wang et al., Role of the amino-terminal domain in regulating interactions of annexin I with membranes: effects of amino-terminal truncation and mutagenesis of the phosphorylation sites. Biochemistry 1994, 33(1):275-282.*
Sudlow et al. The role of lipocortin-1 in dexamethasone-induced suppression of PGE2 and TNFα release from human peripheral blood mononuclear cells. British Journal of Pharmacology 117(7), Apr. 1996. https://bpspubs.onlinelibrary.wiley.com/doi/epdf/10.1111/j.1476-5381.1996.tb15305.x.*
Hayhoe, Richard, P.G. et al., "Annexin 1 and its Bioactive Peptide Inhibit Neutrophil-Endothelium Internations Under Flow: Indication of Disctinct Receptor Involvement", Published online Nov. 8, 2005, Bllod, Mar. 2006, vol. 107, No. 5, pp. 2123-2130.
Hu et al., "Membrane-Induced Folding and Structure of Membrane-Bound Annexin A1 N-Terminal Peptides: Implications for Annexin-Induced Membrane Aggregation", Biophysical Journal vol. 94, Mar. 2008, pp. 1773-1781.
Koehl, Catherine et al; "Compared Action of Neutrophil Proteinase 3 and Elastase on Model Substrates," Journal of Biological Chemistry, Papers in Press, Jan. 21, 2003, vol. 278, No. 15, pp. 12609-12612.
Korkmaz, Brice et al., "Design and Use of Highly Specific Substrates of Neutrophil Elastase and Proteinase 3", American Journal of Respiratory Cell and Molecular Biology, vol. 30, pp. 801-807, 2004, Published in Press Dec. 23, 2003.
Pederzoli-Ribeil et al., "Design and Characterization of a Cleavage-Resistant Annexin A1 Mutant to Control Inflammation in the Microvasculature," Blood, vol. 116, No. 20, pp. 4288-4296, 2010.
Perretti and Dalli, "Exploiting the Annexin A1 Pathway for the Development of Novel Anti-Inflammatory Therapeutics," Br J Pharmacol, vol. 158, pp. 936-946, 2009.
Rescher, Ursula et al. "Proteolytic Cleavage of Annexin 1 by Human Leukocyte Elastase", Biochimica et Biophysica Acta 1763, Sep. 1, 2006, pp. 1320-1324.
Vong, Linda et al., "Annexin 1 Cleavage in Activated Neutrophils, A Pivotal Role for Proteinase 3", Journal of Biological.hemisrty, Papers in Press, Aug. 6, 2007, pp. 29998-30004, Supplementary file, 7 pages.
Walther, Antje et al., "A Novel Ligand of the Formyl Peptide Receptor: Annexin 1 Regulates Neutrophil Extravasation by Interacting with the FPR", Molecular Cell, vol. 5, May 2000, pp. 831-840.
Zhang et al., "Annexin 1 Induced by Anti-Inflammatory Drugs Binds to NF-kappaB and Inhibits Its Activation: Anticancer Effects In Vitro and In Vivo", Cancer Research, Mar. 15, 2010, Vo. 10, No. 6, pp. 2379-2388.

(Continued)

*Primary Examiner* — Maury A Audet
(74) *Attorney, Agent, or Firm* — Greenberg Traurig, LLP; David J. Dykeman; Natalie Salem

(57) ABSTRACT

Polypeptides having homology to regions of the N-terminal 50 residues of human Annexin 1 are provided for medical use as anti-inflammatory agents. Some of the polypeptides have homology to the N-terminal 48 residues of human Annexin 1, especially to residues 2-48 and 11-48 thereof. In some embodiments, properties of these compounds are improved by at least one modification at residues corresponding to residues 11, 22, 25 and/or 36 of human Annexin 1, and/or by C-terminal amidation of the polypeptide. Analogs of amino acids 2-26 of human Annexin 1, especially acetylated at the N-terminus and/or amidated at the C-terminus and having modifications at 11 and/or 22 are also disclosed for medical use as anti-inflammatory agents.

6 Claims, 9 Drawing Sheets
(3 of 9 Drawing Sheet(s) Filed in Color)
Specification includes a Sequence Listing.

(56) References Cited

OTHER PUBLICATIONS

International Search Report and Written Opininon issued in International Application No. PCT/US2012/042699 dated Dec. 17, 2012.
Supplementary European Search Report issued in European Application No. 12799815.1 dated Apr. 10, 2015.
Extended European Search Report issued in European Application No. 12799815.1 dated Mar. 10, 2016.
Dalli et al., "Proresolving and Tissue-Protective Actions of Annexin A1-Based Cleavage-Resistant Peptides are Mediated by Formyl Peptide Receptor 2/Lipoxin A4 Receptor," The Journal of Immunology, 190:6478-6487, May 17, 2013.
Gavins et al., "Formyl-peptide receptor is not involved in the protection afforded by annexin 1 in murine acute myocardial infarct", The FASEB Journal, Oct. 26, 2004.

\* cited by examiner

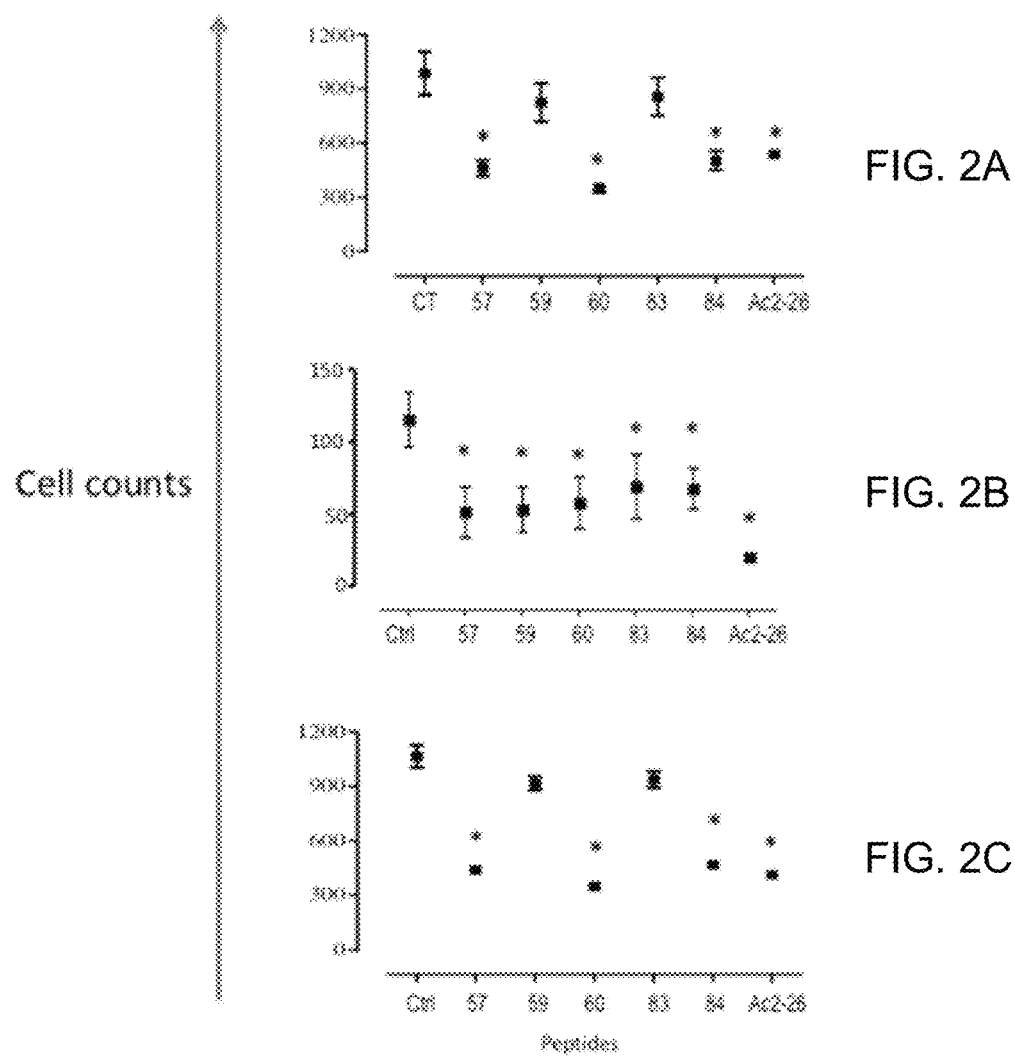

SEQUENCE LISTING

```
<160> NUMBER OF SEQ ID NOS: 16

<210> SEQ ID NO 1
<211> LENGTH: 50
<212> TYPE: PRT
<213> ORGANISM: Human

<400> SEQUENCE: 1

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala
    50

<210> SEQ ID NO 2
<211> LENGTH: 38
<212> TYPE: PRT
<213> ORGANISM: Artificial Sequence
<220> FEATURE:
<223> OTHER INFORMATION: Synthetic sequence having some homology to
      human annexin 1
<220> FEATURE:
<221> NAME/KEY: MISC_FEATURE
<222> LOCATION: (1)..(1)
<223> OTHER INFORMATION: Xaa can be a naturally occurring amino acid
<220> FEATURE:
<221> NAME/KEY: MISC_FEATURE
<222> LOCATION: (12)..(12)
<223> OTHER INFORMATION: Xaa can be a naturally occurring amino acid
<220> FEATURE:
<221> NAME/KEY: MISC_FEATURE
<222> LOCATION: (15)..(15)
<223> OTHER INFORMATION: Xaa can be a naturally occurring amino acid
<220> FEATURE:
<221> NAME/KEY: MISC_FEATURE
<222> LOCATION: (26)..(26)
<223> OTHER INFORMATION: Xaa can be a naturally occurring amino acid

<400> SEQUENCE: 2
```

-continued

```
Xaa Trp Phe Ile Glu Asn Glu Glu Gln Glu Tyr Xaa Gln Thr Xaa Lys
1               5                   10                  15

Ser Ser Lys Gly Gly Pro Gly Ser Ala Xaa Ser Pro Tyr Pro Thr Phe
            20                  25                  30

Asn Pro Ser Ser Asp Val
            35

<210> SEQ ID NO 3
<211> LENGTH: 37
<212> TYPE: PRT
<213> ORGANISM: Artificial Sequence
<220> FEATURE:
<223> OTHER INFORMATION: Synthetic sequence having some homology to
      human annexin 1
<220> FEATURE:
<221> NAME/KEY: MISC_FEATURE
<222> LOCATION: (11)..(11)
<223> OTHER INFORMATION: Xaa can be a naturally occurring amino acid
<220> FEATURE:
<221> NAME/KEY: MISC_FEATURE
<222> LOCATION: (14)..(14)
<223> OTHER INFORMATION: Xaa can be a naturally occurring amino acid
<220> FEATURE:
<221> NAME/KEY: MISC_FEATURE
<222> LOCATION: (25)..(25)
<223> OTHER INFORMATION: Xaa can be a naturally occurring amino acid

<400> SEQUENCE: 3

Trp Phe Ile Glu Asn Glu Glu Gln Glu Tyr Xaa Gln Thr Xaa Lys Ser
1               5                   10                  15

Ser Lys Gly Gly Pro Gly Ser Ala Xaa Ser Pro Tyr Pro Thr Phe Asn
            20                  25                  30

Pro Ser Ser Asp Val
            35

<210> SEQ ID NO 4
<211> LENGTH: 50
<212> TYPE: PRT
<213> ORGANISM: Artificial Sequence
<220> FEATURE:
<223> OTHER INFORMATION: Synthetic sequence having some homology to
      human annexin 1

<400> SEQUENCE: 4

Ala Met Val Ser Glu Phe Leu Lys Gln Ala Trp Phe Ile Glu Asn Glu
1               5                   10                  15

Glu Gln Glu Tyr Val Gln Thr Val Lys Ser Ser Lys Gly Gly Pro Gly
            20                  25                  30

Ser Ala Val Ser Pro Tyr Pro Thr Phe Asn Pro Ser Ser Asp Val Ala
        35                  40                  45

Ala Gly
    50

<210> SEQ ID NO 5
<211> LENGTH: 49
<212> TYPE: PRT
<213> ORGANISM: Artificial Sequence
<220> FEATURE:
<223> OTHER INFORMATION: Synthetic sequence having some homology with
      human annexin 1
<220> FEATURE:
<221> NAME/KEY: MOD_RES
<222> LOCATION: (49)..(49)
<223> OTHER INFORMATION: AMIDATION

<400> SEQUENCE: 5
```

Ala Met Val Ser Glu Phe Leu Lys Gln Ala Trp Phe Ile Glu Asn Glu
1               5                   10                  15

Glu Gln Glu Tyr Val Gln Thr Val Lys Ser Ser Lys Gly Gly Pro Gly
                20                  25                  30

Ser Ala Val Ser Pro Tyr Pro Thr Phe Asn Pro Ser Ser Asp Val Ala
            35                  40                  45

Ala

<210> SEQ ID NO 6
<211> LENGTH: 49
<212> TYPE: PRT
<213> ORGANISM: Artificial Sequence
<220> FEATURE:
<223> OTHER INFORMATION: Synthetic sequence having some homology with
      human annexin 1

<400> SEQUENCE: 6

Ala Met Val Ser Glu Phe Leu Lys Gln Ala Trp Phe Ile Glu Asn Glu
1               5                   10                  15

Glu Gln Glu Tyr Val Gln Thr Val Lys Ser Ser Lys Gly Gly Pro Gly
                20                  25                  30

Ser Ala Val Ser Pro Tyr Pro Thr Phe Asn Pro Ser Ser Asp Val Ala
            35                  40                  45

Ala

<210> SEQ ID NO 7
<211> LENGTH: 47
<212> TYPE: PRT
<213> ORGANISM: Artificial Sequence
<220> FEATURE:
<223> OTHER INFORMATION: Synthetic sequence having some homology with
      human annexin 1
<220> FEATURE:
<221> NAME/KEY: MOD_RES
<222> LOCATION: (47)..(47)
<223> OTHER INFORMATION: AMIDATION

<400> SEQUENCE: 7

Ala Met Val Ser Glu Phe Leu Lys Gln Ala Trp Phe Ile Glu Asn Glu
1               5                   10                  15

Glu Gln Glu Tyr Val Gln Thr Leu Lys Ser Ser Lys Gly Gly Pro Gly
                20                  25                  30

Ser Ala Val Ser Pro Tyr Pro Thr Phe Asn Pro Ser Ser Asp Val
            35                  40                  45

<210> SEQ ID NO 8
<211> LENGTH: 49
<212> TYPE: PRT
<213> ORGANISM: Artificial Sequence
<220> FEATURE:
<223> OTHER INFORMATION: Synthetic sequence having some homology with
      human annexin 1
<220> FEATURE:
<221> NAME/KEY: MOD_RES
<222> LOCATION: (49)..(49)
<223> OTHER INFORMATION: AMIDATION

<400> SEQUENCE: 8

Ala Met Val Ser Glu Phe Leu Lys Gln Ala Trp Phe Ile Glu Asn Glu
1               5                   10                  15

Glu Gln Glu Tyr Val Gln Thr Leu Lys Ser Ser Lys Gly Gly Pro Gly
                20                  25                  30

```
Ser Ala Val Ser Pro Tyr Pro Thr Phe Asn Pro Ser Ser Asp Val Ala
            35                  40                  45

Ala

<210> SEQ ID NO 9
<211> LENGTH: 44
<212> TYPE: PRT
<213> ORGANISM: Artificial Sequence
<220> FEATURE:
<223> OTHER INFORMATION: Synthetic sequence having some homology with
      human annexin 1
<220> FEATURE:
<221> NAME/KEY: MOD_RES
<222> LOCATION: (44)..(44)
<223> OTHER INFORMATION: AMIDATION

<400> SEQUENCE: 9

Ser Glu Phe Leu Lys Gln Ala Trp Phe Ile Glu Asn Glu Glu Gln Glu
1               5                   10                  15

Tyr Val Gln Thr Leu Lys Ser Ser Lys Gly Gly Pro Gly Ser Ala Val
            20                  25                  30

Ser Pro Tyr Pro Thr Phe Asn Pro Ser Ser Asp Val
            35                  40

<210> SEQ ID NO 10
<211> LENGTH: 37
<212> TYPE: PRT
<213> ORGANISM: Artificial Sequence
<220> FEATURE:
<223> OTHER INFORMATION: Synthetic sequence having some homology with
      human annexin 1
<220> FEATURE:
<221> NAME/KEY: MOD_RES
<222> LOCATION: (37)..(37)
<223> OTHER INFORMATION: AMIDATION

<400> SEQUENCE: 10

Trp Phe Ile Glu Asn Glu Glu Gln Glu Tyr Val Gln Thr Leu Lys Ser
1               5                   10                  15

Ser Lys Gly Gly Pro Gly Ser Ala Val Ser Pro Tyr Pro Thr Phe Asn
            20                  25                  30

Pro Ser Ser Asp Val
            35

<210> SEQ ID NO 11
<211> LENGTH: 25
<212> TYPE: PRT
<213> ORGANISM: Artificial Sequence
<220> FEATURE:
<223> OTHER INFORMATION: Synthetic sequence having some homology with
      human annexin 1
<220> FEATURE:
<221> NAME/KEY: MISC_FEATURE
<222> LOCATION: (10)..(10)
<223> OTHER INFORMATION: Xaa may be a naturally occurring amino acid
<220> FEATURE:
<221> NAME/KEY: MISC_FEATURE
<222> LOCATION: (21)..(21)
<223> OTHER INFORMATION: Xaa may be a naturally occurring amino acid

<400> SEQUENCE: 11

Ala Met Val Ser Glu Phe Leu Lys Gln Xaa Trp Phe Ile Glu Asn Glu
1               5                   10                  15

Glu Gln Glu Tyr Xaa Gln Thr Val Lys
            20                  25
```

```
<210> SEQ ID NO 12
<211> LENGTH: 25
<212> TYPE: PRT
<213> ORGANISM: Artificial Sequence
<220> FEATURE:
<223> OTHER INFORMATION: Synthetic sequence having some homology with
      human annexin 1
<220> FEATURE:
<221> NAME/KEY: MOD_RES
<222> LOCATION: (1)..(1)
<223> OTHER INFORMATION: ACETYLATION

<400> SEQUENCE: 12

Ala Met Val Ser Glu Phe Leu Lys Gln Leu Trp Phe Ile Glu Asn Glu
1               5                   10                  15

Glu Gln Glu Tyr Leu Gln Thr Val Lys
            20                  25

<210> SEQ ID NO 13
<211> LENGTH: 25
<212> TYPE: PRT
<213> ORGANISM: Artificial Sequence
<220> FEATURE:
<223> OTHER INFORMATION: Synthetic sequence having some homology with
      human annexin 1
<220> FEATURE:
<221> NAME/KEY: MOD_RES
<222> LOCATION: (1)..(1)
<223> OTHER INFORMATION: ACETYLATION

<400> SEQUENCE: 13

Ala Met Val Ser Glu Phe Leu Lys Gln Asp Trp Phe Ile Glu Asn Glu
1               5                   10                  15

Glu Gln Glu Tyr Asp Gln Thr Val Lys
            20                  25

<210> SEQ ID NO 14
<211> LENGTH: 25
<212> TYPE: PRT
<213> ORGANISM: Artificial Sequence
<220> FEATURE:
<223> OTHER INFORMATION: Synthetic sequence having some homology with
      human annexin 1
<220> FEATURE:
<221> NAME/KEY: MOD_RES
<222> LOCATION: (1)..(1)
<223> OTHER INFORMATION: ACETYLATION

<400> SEQUENCE: 14

Ala Met Val Ser Glu Phe Leu Lys Gln Met Trp Phe Ile Glu Asn Glu
1               5                   10                  15

Glu Gln Glu Tyr Met Gln Thr Val Lys
            20                  25

<210> SEQ ID NO 15
<211> LENGTH: 25
<212> TYPE: PRT
<213> ORGANISM: Artificial Sequence
<220> FEATURE:
<223> OTHER INFORMATION: Synthetic sequence having some homology with
      human annexin 1
<220> FEATURE:
<221> NAME/KEY: MOD_RES
<222> LOCATION: (1)..(1)
<223> OTHER INFORMATION: ACETYLATION

<400> SEQUENCE: 15

Ala Met Val Ser Glu Phe Leu Lys Gln Glu Trp Phe Ile Glu Asn Glu
1               5                   10                  15
```

```
Glu Gln Glu Tyr Glu Gln Thr Val Lys
            20                  25

<210> SEQ ID NO 16
<211> LENGTH: 25
<212> TYPE: PRT
<213> ORGANISM: Artificial Sequence
<220> FEATURE:
<223> OTHER INFORMATION: Synthetic sequence having some homology with
      human annexin 1
<220> FEATURE:
<221> NAME/KEY: MOD_RES
<222> LOCATION: (1)..(1)
<223> OTHER INFORMATION: ACETYLATION

<400> SEQUENCE: 16

Ala Met Val Ser Glu Phe Leu Lys Gln Ile Trp Phe Ile Glu Asn Glu
1               5                   10                  15

Glu Gln Glu Tyr Ile Gln Thr Val Lys
            20                  25
```

ANTI-INFLAMMATORY PHARMACEUTICAL PRODUCTS

RELATED APPLICATIONS

This application is a divisional of U.S. patent application Ser. No. 13/524,381, filed Jun. 15, 2012, which claims the benefit of and priority to U.S. Provisional Application Ser. No. 61/497,270, filed Jun. 15, 2011, the disclosures of all of which are herein incorporated by reference in their entireties.

FIELD

The embodiments disclosed herein relate to anti-inflammatory compounds having defined structural homology to human Annexin 1, to pharmaceutical compositions thereof, and to medical treatments and uses of these compounds and compositions as anti-inflammatory agents.

BACKGROUND

The Annexin super-family consists of 13 calcium phospholipid binding proteins with significant biological and structural homology. Annexins are structurally divided into a highly conserved core domain and a variable N-terminal domain. Annexin 1 (ANXA1, 37 kDa) is an anti-inflammatory protein that inhibits extravasation of blood-borne polymorphonuclear leukocyte (PMN) into the surrounding tissue. The protein binds to the FPR2 (or FPR-L1) receptor, where it initiates a cascade of signaling events. Following an inflammatory stimulus, migration of blood-borne polymorphonuclear leukocyte (PMN) into the surrounding tissue takes place. Transmigration or extravasation of PMN is regulated by mediators such as adhesion molecules, cytokines and proteases, which control the pro-inflammatory and anti-inflammatory processes. The disruptive potential of the PMN is high and potentially self-damaging. Thus, controlling extravasation of PMN and the inflammatory response is important.

For therapeutic purposes as an anti-inflammatory agent, the full Annexin 1 protein has numerous disadvantages relative to functional fragments or modified versions thereof. The large size of the protein makes it more difficult to deliver by techniques that are possible with a smaller polypeptide (e.g. transdermally or transmucosally). For use to treat inflammation of the eyes, a smaller molecule is expected to be better able to penetrate the corneal epithelium. Also, susceptibility to proteolytic degradation is a particular concern for all peptide pharmaceuticals, especially large ones and especially if oral delivery (preferred by many patients) is contemplated.

Some Annexin 1 derivatives lacking significant regions on the N-terminal side of the polypeptide have been shown to lack significant activity in some assays of inflammation and mediator release, whereas the full length N-terminus N-acetyl Annexin 1 (2-26) was deemed biologically active in several systems. A number of peptides primarily derived from the unique N-terminal portion of the Annexin 1 protein have been shown to possess anti-inflammatory properties.

One of the most extensively studied Annexin A1 peptides is peptide Ac2-26, which mimics the 2nd to the 26th amino acids of the 54-amino acid N-terminal region. Like the Ac1-188 fragment (and the native protein), it has an N-terminal acetylation to increase its stability, and possibly its half-life. It has been show that Annexin 1 and its N-terminal peptide (Ac2-26) exert the majority of their anti-inflammatory action through the FPR2/Lipoxin A4 (FPR2/Alx) receptor. In vivo the Ac2-26 peptide has been shown to exert an anti-inflammatory effect in models of myocardial ischaemia reperfusion (I/R), mesentery I/R, glycogen peritonitis and IL1 airpouch, where it was reported to significantly reduce the recruitment of neutrophils to the site of injury/inflammation. The anti-inflammatory properties of this peptide are not just restricted to acute models of inflammation. In an arthritis model, intra-articular administration of the Ac2-26 peptide was shown to reduce disease severity through a reduction in neutrophil recruitment.

Shorter versions of the Ac2-26 peptide, such as peptides Ac2-12 and Ac2-6, have also been shown to elicit some degree of anti-inflammatory effects in acute models of inflammation. Work conducted by a number of laboratories has shown that a peptide derived from a region completely independent of the N-terminal of the Annexin A1 protein, more precisely amino acids 247-253—in the third repeat of the core region of the protein—referred to as antiflammin-2 (AF2), also possesses anti-inflammatory properties.

SUMMARY

The embodiments disclosed herein relate to anti-inflammatory pharmaceutical products, and more particularly to polypeptides, pharmaceutical compositions comprising the polypeptides, and methods of treating or preventing inflammation. Anti-inflammatory pharmaceutical products of the present disclosure have qualities including, but not limited to, good anti-inflammatory efficacy, stability and/or ease of administration, as detailed herein.

According to aspects illustrated herein, there is provided a polypeptide as set forth in SEQ ID NO: 4 ("UGP021").
According to aspects illustrated herein, there is provided a polypeptide as set forth in SEQ ID NO: 5 ("UGP022").
According to aspects illustrated herein, there is provided a polypeptide as set forth in SEQ ID NO: 6 ("UGP024").
According to aspects illustrated herein, there is provided a polypeptide as set forth in SEQ ID NO: 7 ("UGP025").
According to aspects illustrated herein, there is provided a polypeptide as set forth in SEQ ID NO: 8 ("UGP026").
According to aspects illustrated herein, there is provided a polypeptide as set forth in SEQ ID NO: 9 ("UGP027").
According to aspects illustrated herein, there is provided a polypeptide as set forth in SEQ ID NO: 10 ("UGP028").
According to aspects illustrated herein, there is provided a polypeptide as set forth in SEQ ID NO: 11.
According to aspects illustrated herein, there is provided a polypeptide as set forth in SEQ ID NO: 12 ("Pep57").
According to aspects illustrated herein, there is provided a polypeptide as set forth in SEQ ID NO: 13 ("Pep59").
According to aspects illustrated herein, there is provided a polypeptide as set forth in SEQ ID NO: 14 ("Pep84").
According to aspects illustrated herein, there is provided a polypeptide as set forth in SEQ ID NO: 15 ("Pep60").
According to aspects illustrated herein, there is provided a polypeptide as set forth in SEQ ID NO: 16 ("Pep83").
According to aspects illustrated herein, there is provided a polypeptide having 47-50 amino acids and including within its molecular structure a region of homology that has at least 90 percent identity to residues 2-48 of SEQ ID NO: 1, wherein residue 24 of the polypeptide corresponds to residue 25 of SEQ ID NO: 1, and wherein residue 24 of the polypeptide is not valine. In an embodiment, the region of homology of the polypeptide has at least 94 percent identity to residues 2-48 of SEQ ID NO: 1. In an embodiment, the region of homology of the polypeptide is 100 percent identical to residues 2-23 of SEQ ID NO: 1.

According to aspects illustrated herein, there is provided a polypeptide having 25-26 amino acids and including within its molecular structure a region of homology that has at least 90 percent identity to residues 2-26 of SEQ ID NO: 1, wherein residue 10 of the polypeptide corresponds to residue 11 of SEQ ID NO: 1, wherein residue 10 of the polypeptide is any amino acid except for alanine, and wherein residue 21 of the peptide is any amino acid except for valine.

According to aspects illustrated herein, there is provided a polypeptide having 37-45 amino acids and including within its molecular structure a region of homology that is 100 percent identical to residues 12-24 of SEQ ID NO: 1 and 100 percent identical to residues 26-48 of SEQ ID NO:1, wherein either residue 14 of the polypeptide corresponds to residue 25 of SEQ ID NO: 1 and is not valine, or wherein residue 21 of the polypeptide corresponds to residue 25 of SEQ ID NO: 1 and is not valine.

According to aspects illustrated herein, there is provided a polypeptide having 47-50 amino acids and including within its molecular structure a region of homology that is 100 percent identical to residues 2-48 of SEQ ID NO: 1, wherein the polypeptide is amidated at its C-terminus.

According to aspects illustrated herein, there is provided a polypeptide having from 37 to 51 amino acid residues and including within its molecular structure a region of homology that is at least 90 percent identical to SEQ ID NO: 2, wherein the homology region of the polypeptide has at least one of the following characteristics: (a) the residue of the polypeptide corresponding to residue 1 of SEQ ID NO: 2 is not alanine, (b) the residue of the polypeptide corresponding to residue 12 of SEQ ID NO: 2 is not valine, (c) the residue of the polypeptide corresponding to residue 15 of SEQ ID NO: 2 is not valine or (d) the residue of the polypeptide corresponding to residue 26 of SEQ ID NO: 2 is not valine.

According to aspects illustrated herein, there is provided a polypeptide having 47-48 amino acids and at least 90 percent identity residues 1-48 of SEQ ID NO: 1.

According to aspects illustrated herein, there is provided a polypeptide having from 47 to 51 amino acid residues and including within its molecular structure a region of 47 amino acid residues that is 100 percent identical to residues 2-48 of human Annexin 1.

According to aspects illustrated herein, there is provided a polypeptide having from 49 to 51 amino acid residues and including within its molecular structure a region of 47 amino acid residues that is 100 percent identical to residues 2-48 of human Annexin 1.

According to aspects illustrated herein, there is provided a polypeptide having at least 96 percent identity to SEQ ID NO: 11 wherein either residue 10 is not alanine or residue 21 is not valine. In some embodiments, both residue 10 is not alanine and residue 21 is not valine.

According to aspects illustrated herein, there is provided a polypeptide having an amino acid sequence as set forth in SEQ ID NO: 11 wherein either residue 10 is not alanine or residue 21 is not valine. In some embodiments, both residue 10 is not alanine and residue 21 is not valine.

According to aspects illustrated herein, there is provided a method of treating or preventing inflammation comprising administering to a patient in need of such treatment or prevention a therapeutically effective amount of an anti-inflammatory polypeptide of the present disclosure.

According to aspects illustrated herein, a polypeptide of the present disclosure can be used in the manufacture of a medicament for the treatment or prevention of inflammation. In an embodiment, the medicament includes one or more pharmaceutically acceptable excipients, diluents or carriers.

In an embodiment, a pharmaceutical composition of the present disclosure includes, but is not limited to, a composition in the form of a tablet or a capsule comprising at least one pharmaceutically acceptable acid, wherein the acid is present in the tablet or capsule in a quantity which, if the tablet or capsule, were added to 10 milliliters of 0.1M aqueous sodium bicarbonate solution, would be sufficient to lower the pH of the solution to no higher than 5.5. Other preferences for dosage forms are set forth infra.

Both veterinary and human use are contemplated within the scope of the present disclosure. Dosages discussed herein are expected to be the same for human and veterinary uses, except that a pro rata adjustment may be made based on the relative weight of the animal to which the pharmaceuticals of the present disclosure are to be administered.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 1A is a representative blot for p-ERK and t-ERK. FIG. 1B shows densitometry results relating the p-ERK to the t-ERK levels.

FIGS. 2A-2C are a series of charts reporting data from flow chamber analysis to determine the inhibitory capability of five polypeptides of the present disclosure (Pep57 (SEQ ID NO:12); Pep59 (SEQ ID NO:13), Pep60 (SEQ ID NO:15), Pep83 (SEQ ID NO:16) and Pep84 (SEQ ID NO:14)) and Ac-ANAX1(2-26)-OH to reduce PMN interaction to an activated HUVEC monolayer. FIG. 2A shows quantification of the degree of PMN interaction with the HUVECs as PMN capture. FIG. 2B shows quantification of the degree of PMN interaction with the HUVECs as PMN adhesion. FIG. 2C shows quantification of the degree of PMN interaction with the HUVECs as rolling.

FIG. 3A shows the cell count and FIG. 3B shows the effects when the GR1+ve cells were taken into account.

DETAILED DESCRIPTION

Figure 1A:
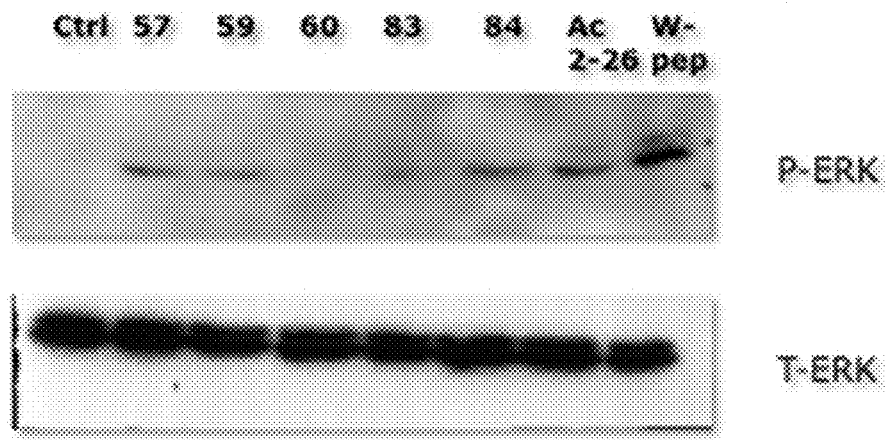
FIG. 1A and FIG. 1B show western blotting analysis comparing p-ERK activation potency through the FPR2 receptor for five polypeptides of the present disclosure (Pep57 (SEQ ID NO:12); Pep59 (SEQ ID NO:13), Pep60 (SEQ ID NO:15), Pep83 (SEQ ID NO:16) and Pep84 (SEQ ID NO:14)) relative to Ac-ANAX1(2-26)-OH.

In the attached sequence listing:

SEQ ID NO: 1 is the first 50 amino acids of human Annexin 1.

SEQ ID NO: 2 is amino acids 11-48 of human Annexin 1, modified with variables that may be any naturally occurring amino acid at positions 11, 22, 25 and 36 (relative to Annexin 1) which are equivalent to positions 1, 12, 15 and 26 of SEQ ID NO:2.

SEQ ID NO: 3 is almost identical to SEQ ID NO:2, differing only in that SEQ ID NO:3 omits the first residue of SEQ ID NO:2.

SEQ ID NO: 4 is an embodiment of a polypeptide of the present disclosure, UGP021. UGP021 is 50 amino acids in length. UGP021 is amino acids 2-50 of human Annexin 1, wherein position 50 of the polypeptide is glycine. In an embodiment, UGP021 is referred to as ANXA1(2-50) Gly51-OH.

SEQ ID NO: 5 is an embodiment of a polypeptide of the present disclosure, UGP022. UGP022 is 49 amino acids in length. UGP022 is amino acids 2-50 of human Annexin 1, wherein the polypeptide is amidated at its C-terminus. In an embodiment, UGP022 is referred to as ANXA1(2-50)-$NH_2$.

SEQ ID NO: 6 is an embodiment of a polypeptide of the present disclosure, UGP024. UGP024 is 49 amino acids in length. UGP024 is amino acids 2-50 of human Annexin 1. In an embodiment, UGP024 is referred to as ANXA1(2-50)-OH.

SEQ ID NO: 7 is an embodiment of a polypeptide of the present disclosure, UGP025. UGP025 is 47 amino acids in length. UGP025 is amino acids 2-48 of human Annexin 1, wherein the polypeptide is amidated at its C-terminus, and wherein residue 24 of the polypeptide is leucine instead of corresponding reside 25 of SEQ ID NO: 1 which is valine. In an embodiment, UGP025 is referred to as Leu25-ANXA1 (2-48)-$NH_2$.

SEQ ID NO: 8 is an embodiment of a polypeptide of the present disclosure, UGP026. UGP026 is 49 amino acids in length. UGP026 is amino acids 2-50 of human Annexin 1, wherein the polypeptide is amidated at its C-terminus, and wherein residue 24 of the polypeptide is leucine instead of corresponding reside 25 of SEQ ID NO:1 which is valine. In an embodiment, UGP026 is referred to as Leu25-ANXA1 (2-50)-$NH_2$.

SEQ ID NO:9 is an embodiment of a polypeptide of the present disclosure, UGP027. UGP027 is 44 amino acids in length. UGP027 is amino acids 5-48 of human Annexin 1, wherein the polypeptide is amidated at its C-terminus, and wherein residue 21 of the polypeptide is leucine instead of corresponding reside 25 of SEQ ID NO: 1 which is valine. In an embodiment, UGP027 is referred to as Leu25-ANXA1 (5-48)-$NH_2$.

SEQ ID NO:10 is an embodiment of a polypeptide of the present disclosure, UGP028. UGP028 is 37 amino acids in length. UGP028 is amino acids 12-48 of human Annexin 1, wherein the polypeptide is amidated at its C-terminus, and wherein residue 14 of the polypeptide is leucine instead of corresponding reside 25 of SEQ ID NO: 1 which is valine. In an embodiment, UGP028 is referred to as Leu25-ANXA1 (12-48)-$NH_2$.

SEQ ID NO: 11 is an embodiment of a polypeptide of the present disclosure. SEQ ID NO: 11 is 25 amino acids in length. SEQ ID NO: 11 is amino acids 2-26 of human Annexin 1, modified with variables that may be any naturally occurring amino acid at residue 10 and 21 of the polypeptide (which are equivalent to positions 11 and 22 of SEQ ID NO:1).

SEQ ID NO:12 is an embodiment of a polypeptide of the present disclosure, Pep57. Pep57 is 25 amino acids in length. Pep57 is amino acids 2-26 of human Annexin 1, wherein residue 10 of the polypeptide is leucine instead of corresponding reside 11 of SEQ ID NO:1 which is alanine, wherein residue 21 of the polypeptide is leucine instead of corresponding residue 22 of SEQ ID NO:1 which is valine, and wherein residue 1 of the polypeptide is acetylated. In an embodiment, Pep57 is referred to as Leu11,22-Ac-ANAX1 (2-26)-OH.

SEQ ID NO: 13 is an embodiment of a polypeptide of the present disclosure, Pep59. Pep59 is 25 amino acids in length. Pep59 is amino acids 2-26 of human Annexin 1, wherein residue 10 of the polypeptide is aspartic acid instead of corresponding reside 11 of SEQ ID NO: 1 which is alanine, wherein residue 21 of the polypeptide is aspartic acid instead of corresponding residue 22 of SEQ ID NO:1 which is valine, and wherein residue 1 of the polypeptide is acetylated. In an embodiment, Pep59 is referred to as Asp11,22-Ac-ANAX1(2-26)-OH.

SEQ ID NO:14 is an embodiment of a polypeptide of the present disclosure, Pep84. Pep84 is 25 amino acids in length. Pep84 is amino acids 2-26 of human Annexin 1, wherein residue 10 of the polypeptide is methionine instead of corresponding reside 11 of SEQ ID NO:1 which is alanine, wherein residue 21 of the polypeptide is methionine instead of corresponding residue 22 of SEQ ID NO:1 which is valine, and wherein residue 1 of the polypeptide is acetylated. In an embodiment, Pep84 is referred to as Met11,22-Ac-ANAX1(2-26)-OH.

SEQ ID NO: 15 is an embodiment of a polypeptide of the present disclosure, Pep60. Pep60 is 25 amino acids in length. Pep60 is amino acids 2-26 of human Annexin 1, wherein residue 10 of the polypeptide is glutamic acid instead of corresponding reside 11 of SEQ ID NO:1 which is alanine, wherein residue 21 of the polypeptide is glutamic acid instead of corresponding residue 22 of SEQ ID NO:1 which is valine, and wherein residue 1 of the polypeptide is acetylated. In an embodiment, Pep60 is referred to as Glu11,22-Ac-ANAX1(2-26)-OH.

SEQ ID NO: 16 is an embodiment of a polypeptide of the present disclosure, Pep83. Pep83 is 25 amino acids in length. Pep83 is amino acids 2-26 of human Annexin 1, wherein residue 10 of the polypeptide is isoleucine instead of corresponding reside 11 of SEQ ID NO:1 which is alanine, wherein residue 21 of the polypeptide is isoleucine instead of corresponding residue 22 of SEQ ID NO:1 which is valine, and wherein residue 1 of the polypeptide is acetylated. In an embodiment, Pep83 is referred to as Ile11,22-Ac-ANAX1(2-26)-OH.

Except where otherwise noted or where apparent from context, dosages herein refer to weight of active compounds unaffected by pharmaceutical excipients, diluents, carriers or other ingredients, although such additional ingredients are desirably included, as discussed in more detail infra. Any dosage form (capsule, tablet, injection or the like) commonly used in the pharmaceutical industry for delivery of peptide active agents is appropriate for use herein, and the terms "excipient", "diluent", or "carrier" includes such non-active ingredients as are typically included, together with active ingredients in such dosage form in the industry. An oral dosage form is discussed in more detail infra, but is not to be considered the exclusive mode of administering the active agents of the present disclosure. In some embodiments, a mixture of two or more of the polypeptide active agents of the present disclosure may be utilized in the same pharmaceutical composition or dosage form.

As used herein, the term "polypeptide" refers to a polymer of amino acids and is not limited to a specific length of the molecule. The term includes peptides, oligopeptides, and proteins. The term "polypeptide" also includes modifications of the polypeptide, for example, amidations, glycosylations, acetylations, phosphorylations, cyclisations and the like. Included within the definition are, for example, polypeptides containing one or more analogues of an amino acid (including, for example, unnatural amino acids, etc.), polypeptides with substituted linkages, as well as other modifications known in the art, both naturally occurring and non-naturally occurring. The polypeptide may be produced by any polypeptide synthesis known in the art, including but not limited to chemical synthesis or by recombinant DNA techniques.

As used herein, the term "percent identity" refers to amino acid sequence without regard to whether a given amino acid is modified with an additional substituent (other than an additional amino acid). For example cysteine is considered identical to acetylcysteine for this purpose. Likewise, for this purpose, a cysteine that has formed a disulfide bridge with another cysteine would be considered identical to a cysteine that has not formed such a bridge. As those of skill in the art will appreciate, peptides having a plurality of cysteine residues frequently form a disulfide bridge between two such cysteine residues. All such peptides set forth herein are defined as optionally including one or more such disulfide bridges. As used herein, the term "Percent identity" also contemplates differences in peptide size. For example, a 34-residue peptide that is otherwise identical to a 33-residue peptide (except for its one additional amino acid) is considered herein to be 97 percent identical to the 33-residue peptide.

As used herein, reference to "inflammation" or "inflammatory response/disease" refers to any inflammatory response or disease, including but not limited to inflammation of the eye, gout, gouty arthritis, rheumatoid arthritis, asthma, reperfusion injury or damage, stroke, myocardial infarction, septic shock, or an inflammatory skin disorder, such as psoriasis or eczema.

Any preferences stated herein may be used in combination with any other preferences stated herein except where it is apparent from context that inconsistency would result.

Applicants have discovered some significant advantages in longer analogs with substantial homology to residues 2-48 or 2-50 of human Annexin 1, especially polypeptides having from 37-51 residues and including a region of substantial homology to residues 11-48 of human Annexin 1, especially a region of substantial homology to SEQ ID NO: 2.

In an embodiment, the homology region of the polypeptide of the present disclosure corresponding to SEQ ID NO:2 has at least one (and in some embodiments, more) of the following characteristics: (a) the residue of the polypeptide corresponding to residue 1 of SEQ ID NO: 2 is arginine, (b) the residue of the polypeptide corresponding to residue 12 of SEQ ID NO: 2 is lysine, (c) the residue of the polypeptide corresponding to residue 15 of SEQ ID NO: 2 is leucine or (d) the residue of the polypeptide corresponding to residue 26 of SEQ ID NO: 2 is lysine. In an embodiment, the homology region is at least 94 percent identical to SEQ ID NO: 2, and in some embodiments 100 percent identical.

In an embodiment, the homology region of the polypeptide corresponding to SEQ ID NO: 2 differs from SEQ ID NO:2 in that the polypeptide corresponding to residue 15 of SEQ ID NO: 2 is not valine, and in some embodiments is leucine.

In an embodiment, when a polypeptide of the present disclosure has 47-48 amino acids and at least 90 percent identity to residues 1-48 of SEQ ID NO:1, the polypeptide has at least one (and in some embodiments, more) of the following characteristics: (a) the residue of the polypeptide corresponding to residue 11 of SEQ ID NO:1 is not alanine (and in some embodiments is arginine), (b) the residue of the polypeptide corresponding to residue 22 of SEQ ID NO:1 is not valine (and in some embodiments is lysine), (c) the residue of the polypeptide corresponding to residue 25 of SEQ ID NO:1 is not valine (and in some embodiments is leucine) or (d) the residue of the polypeptide corresponding to residue 36 of SEQ ID NO:1 is not valine (and in some embodiments is lysine).

While peptides of the present disclosure may exist in free acid form, in some polypeptides of the present disclosure the C-terminal amino acid is amidated. In an embodiment, such amidation contributes to the effectiveness and/or bioavailability of the peptide. In an embodiment, a C-terminal amidated polypeptide of the present invention, such as UGP022 (SEQ ID NO:5), shows better in vitro results than with a free acid precursor, such as UGP021 (SEQ ID NO: 4). Without intending to be bound by theory, it is possible that such polypeptides are more stable because the amide group confers some resistance to action of carboxypeptidases.

Peptides of the present disclosure can be acetylated at the N-terminus, especially regarding analogs of Annexin 1 (2-26) such as the polypeptide of SEQ ID NO: 11. In an embodiment, residues 10 and 21 of SEQ ID NO:11 are independently selected from aspartic acid, lysine, methionine, leucine, isoleucine and glutamic acid. In an embodiment, residues 10 and 21 of SEQ ID NO:11 are independently selected from leucine, aspartic acid, methionine, isoleucine and glutamic acid. In an embodiment, residues 10 and 21 of SEQ ID NO: 11 are independently selected from leucine, aspartic acid and methionine. In an embodiment, amino acids at positions 10 and 21 of SEQ ID NO: 11 are identical.

As described herein, the UGP021 peptide of the present disclosure (SEQ ID NO: 4) and the UGP024 peptide of the present disclosure (SEQ ID NO: 6) are found to be more potent than Ac-ANXA1(2-26)-OH and full length ANXA1. These peptides, UGP021 (SEQ ID NO:4) and UGP024 (SEQ ID NO:6), have been evaluated for their ability to inhibit neutrophilendothelium interactions using a flow-chamber assay and have been tested in vivo using a mouse air-pouch inflammation model. Unexpectedly, the UGP022 peptide of the present disclosure (SEQ ID NO: 5) (C-terminal amide) was found to be more potent than either the UGP021 peptide of the present disclosure (SEQ ID NO: 4) or the UGP024 (SEQ ID NO: 6) peptide of the present disclosure in these assays.

In an attempt to improve the potency and increase the half-life of the UGP022 peptide of the present disclosure (SEQ ID NO: 5), a series of in vitro PR3 and FINE digests were conducted. The major cleavage sites for both serine proteases cleaved the UGP022 (SEQ ID NO: 5) peptide of the present disclosure at Ala 10 (Ala11 relative to Annexin 1) and Val 21 (Val22 relative to Annexin 1), however Val 35 (Val36 relative to Annexin 1) was only cleaved by FINE. Unexpectedly both proteases cleaved the UGP022 peptide (SEQ ID NO: 5) of the present disclosure at Val 24 (Val25 relative to Annexin 1). This cleavage site is not believed to have been identified in the literature.

Two Leu24 (Leu25 relative to Annexin 1) analogues were prepared, the UGP025 peptide of the present disclosure (SEQ ID NO: 7) and the UGP026 peptide of the present disclosure (SEQ ID NO: 8). It was demonstrated that both peptides, UGP025 (SEQ ID NO: 7) and UGP026 (SEQ ID NO: 8), were more resistant to PR3 and FINE than the UGP022 peptide of the present disclosure (SEQ ID NO: 5).

Degradation tests of three polypeptides of the present disclosure, UGP022 (SEQ ID NO:5), UGP025 (SEQ ID NO:7) and UGP026 (SEQ ID NO:8) in the presence of PR3, a protease implicated in the in vivo cleavage of Annexin 1, indicated better stability for polypeptides with Leucine substitution at position 24 relative to a polypeptide lacking that feature. Position 24 corresponds to position 25 of Annexin 1 because all tested polypeptides lack the methionine at position 1 of natural Annexin. A 47-residue polypeptide outperformed an otherwise identical 49-residue polypeptide. Similar results were obtained in degradation tests in the presence of FINE.

Of the Ac2-26 peptide variants tested, three peptides of the present disclosure were observed to lead to downstream signaling via the FPR family of receptors, namely the Pep57 peptide (SEQ ID NO: 12) of the present disclosure, the Pep59 peptide (SEQ ID NO: 13) of the present disclosure and the Pep84 peptide (SEQ ID NO: 14) of the present disclosure. It was shown that Pep57 (SEQ ID NO: 12) and Pep84 (SEQ ID NO: 14) significantly inhibited PMN-HUVEC interactions in the flow chamber model with activity down to 10 pM. When tested in vivo, in the air-pouch model, both peptides displayed anti-inflammatory properties by significantly inhibiting leukocyte infiltration, with Pep84 (SEQ ID NO: 14) inhibiting this inflammatory readout to a larger extent.

Figure 1B:
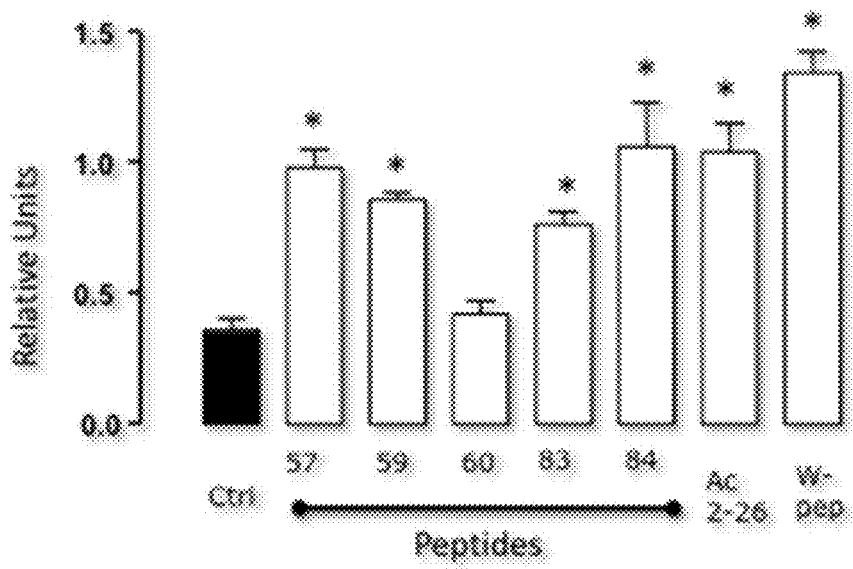

The experiments whose results are reported in FIG. 1A and FIG. 1B were directed to determining which of the five polypeptides tested (Pep57 (SEQ ID NO: 12); Pep59 (SEQ ID NO: 13), Pep60 (SEQ ID NO: 15), Pep83 (SEQ ID NO: 16) and Pep84 (SEQ ID NO: 14)) best activated the p-ERK through the FPR2 receptor, similar to Ac-ANAX1(2-26)-OH, the parent peptide. The HEK-FPR2 cells were co-incubated with 10 µM of the novel Ac2-26 peptides for 8 minutes following which the cell were lysed and resuspended in cell lysis solution. Then 100 ng of total protein were loaded on to 10% polyacrylamide gel. Following electrophoresis, transfer and blocking the membrane was first probed with an anti p-ERK antibody and then stripped and reprobed with and anti total ERK antibody. Whilst the t-ERK blot shows equal amounts of ERK in all the samples the p-ERK activated was observed to be highest with Pep57 (SEQ ID NO: 12), Pep59 (SEQ ID NO: 13) and Pep84 (SEQ ID NO:14), similar to the activation caused by the parent Ac2-26 and less then the second control, the W-peptide. FIG. 1A is a representative blot for p-ERK and t-ERK and FIG. 1B shows densitometry results relating the p-ERK to the t-ERK levels. Data presented as mean and SEM of 3 distinct experiments with one way ANOVA employed for statistical analysis. (*=P<0.05 vs. CT).

FIGS. 2A-2C are a series of charts reporting data from flow chamber analysis to determine the inhibitory capability of five polypeptides (Pep57 (SEQ ID NO: 12); Pep59 (SEQ ID NO: 13), Pep60 (SEQ ID NO: 15), Pep83 (SEQ ID NO: 16) and Pep84 (SEQ ID NO: 14)) of the present disclosure and Ac-ANAX1(2-26)-OH to reduce PMN interaction to an activated HUVEC monolayer. PMNs ($5\times10^6$) were incubated with 10 µM of the various peptides for 10 min at 37° C. The PMNs were then flowed for 8 min at 1 dyne/cm$^2$, prior to quantifying the degree of PMN interaction with the HUVECs, both as PMN capture (FIG. 2A), adhesion (FIG. 2B) and rolling (FIG. 2C). The results highlights the fact that only Pep57 (SEQ ID NO: 12), Pep60 (SEQ ID NO: 15) and Pep84 (SEQ ID NO: 14) display inhibitory properties in this assay. Data are mean±SEM of 3 independent experiments (with distinct PMN and HUVEC preparations); *=P<0.05 vs. CT group, data analyzed using one way ANOVA. Pep57 (SEQ ID NO: 12) and Pep84 (SEQ ID NO:14) displayed inhibitory properties similar to those observed in the parent Ac2-26 peptide, in line with the p-ERK data. Pep59 (SEQ ID NO: 13), which also showed a very high p-ERK activation potential, did not display any inhibitory properties in this assay, whereas, on the other hand Pep60 (SEQ ID NO: 15), which was not that effective to phosphorylate ERK, displayed potent inhibitory properties similar to those displayed by the parent Ac2-26 peptide.

Figure 3A:
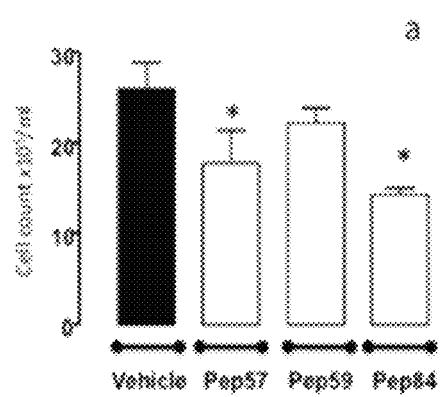
FIG. 3A and FIG. 3B are a series of bar charts comparing the anti-inflammatory effects of three polypeptides (Pep57 (SEQ ID NO:12); Pep59 (SEQ ID NO:13) and Pep84 (SEQ ID NO:14)) of the present disclosure versus a vehicle-only control.
Figure 3B:
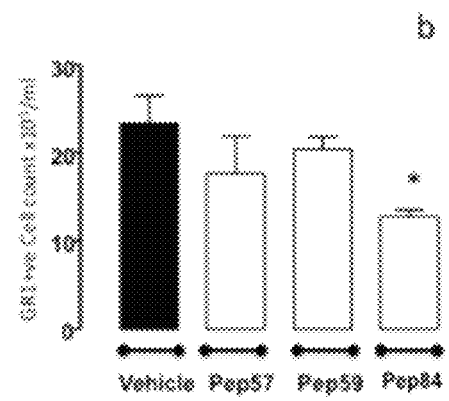

FIG. 3A and FIG. 3B are a series of bar charts comparing the anti-inflammatory effects of three polypeptides (Pep57 (SEQ ID NO: 12); Pep59 (SEQ ID NO: 13) and Pep84 (SEQ ID NO: 14)) of the present disclosure versus a vehicle-only control. Mice received 200 µl i.v. of saline+DMSO or a dose of 50 µg per animal of one of the three Ac2-26 derived peptides, immediately before the local injection of mouse IL-1β into 6-day-old airpouches. The extent of cell migration was determined 4 h later, following airpouch washing and staining of migrated cells with Gr1 marker. When cells were counted (FIG. 3A) Pep57 (SEQ ID NO: 12) and Pep84 (SEQ ID NO: 14) were observed to display anti-inflammatory properties, with Pep57 (SEQ ID NO:12) losing this observed effect when the GR1+ve cells were taken into account (FIG. 3B). Data are mean±SEM of 5 mice per group. *P<0.05 vs. vehicle group (one way ANOVA). Pep57 (SEQ ID NO: 12) and Pep84 (SEQ ID NO: 14) displayed inhibitory potential in the model. Pep84 (SEQ ID NO: 14) was the more potent.

Figure 4A:
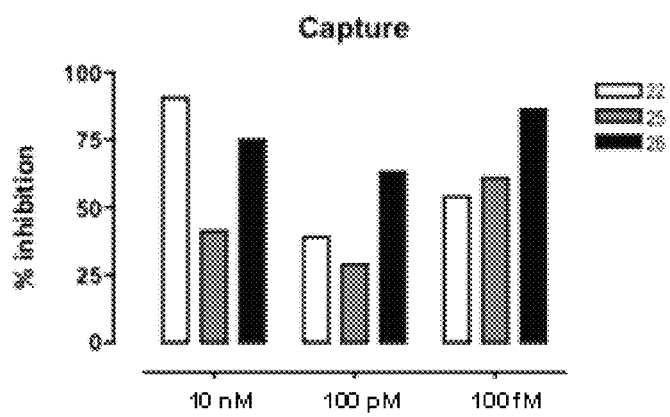
FIGS. 4A-4C are a series of bar charts reporting percent inhibition provided by three polypeptides (UGP022 (SEQ ID NO:5); UGP025 (SEQ ID NO:7) and UGP026 (SEQ ID NO:8)) of the present disclosure, at different concentrations, on three different parameters (capture—FIG. 4A; rolling—FIG. 4B; and adhesion—FIG. 4C).
Figure 4B:
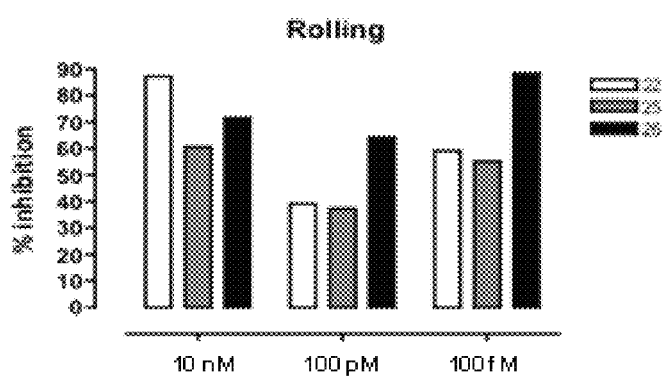
Figure 4C:
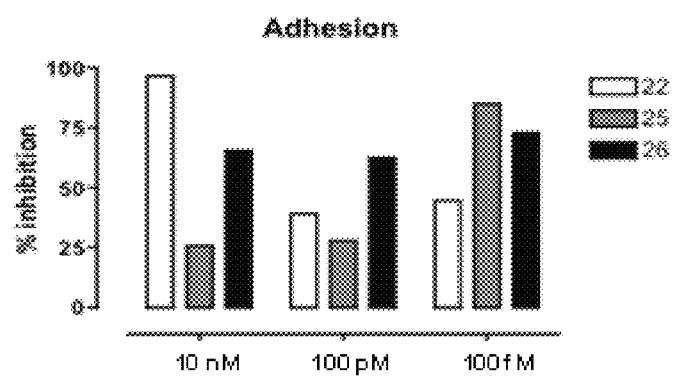

FIGS. 4A-4C make a direct comparison of the activities of UGP022 (SEQ ID NO:5), UGP025 (SEQ ID NO: 7) and UGP026 (SEQ ID NO: 8) in the flow chamber assay, presenting the degree of inhibition on the three parameters under analysis (capture (FIG. 4A); rolling (FIG. 4B) and adhesion (FIG. 4C)). All three UGP peptides are able to reduce the number of human PMNs interacting with an activated endothelium, acting specifically through the FPR2 receptor. Although UGP025 (SEQ ID NO: 7) is less active at the higher concentrations tested, it seems to be slightly more active at the 100 fM concentration when compared to the UGP022 peptide (SEQ ID NO: 5).

In recent years important pro-resolving properties have been ascribed to Annexin A1, namely the induction of phagocytosis of apoptotic cells by macrophages and cells alike. This effect is also reliant on FPR2 and shared with other important pro-resolving mediators including the lipoxins and the resolvins. Experiments were performed to determine whether UGP022 (SEQ ID NO: 5) and derivatives could mimic also this effect of Annexin A1, in view of the potency displayed in a variety of biological assays.

Figure 5:
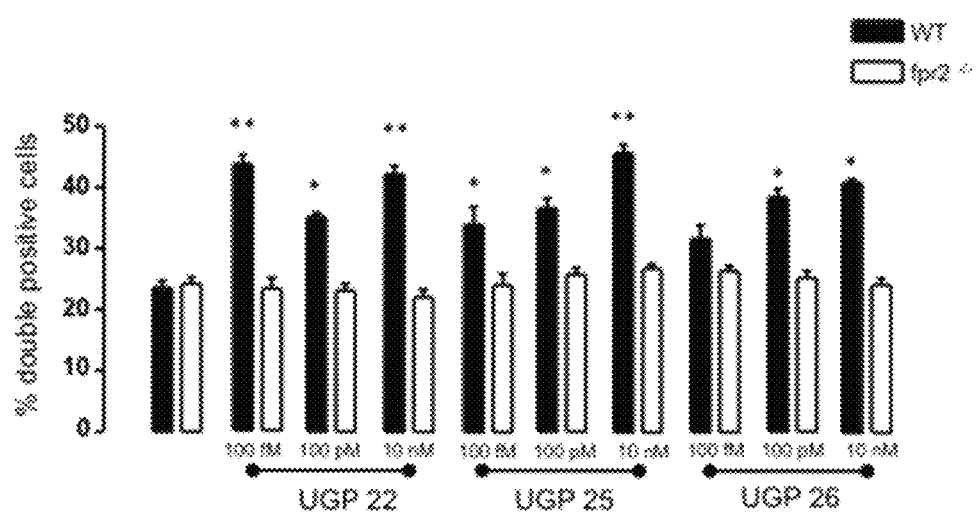
FIG. 5 is a series of bar charts reporting the ability of three polypeptides (UGP022 (SEQ ID NO:5); UGP025 (SEQ ID NO:7) and UGP026 (SEQ ID NO:8))_of the present disclosure, at different concentrations, to mimic an Annexin A1 property of inducing phagocytosis of apoptotic cells.

FIG. 5 is a series of bar charts reporting the ability of three polypeptides (UGP022 (SEQ ID NO:5); UGP025 (SEQ ID NO:7) and UGP026 (SEQ ID NO:8)) of the present disclosure, at different concentrations, to mimic an Annexin A1 property of inducing phagocytosis of apoptotic cells. It can be seen from FIG. 5 that all three peptides (UGP022 (SEQ ID NO:5), UGP025 (SEQ ID NO:7) and UGP026 (SEQ ID NO:8)) promoted phagocytosis of the apoptotic PMN, with UGP022 (SEQ ID NO:5) displaying the higher ability to induce this process. Regarding some of the longer Annexin A1 N-terminal peptides (e.g 49 and 47 residue polypeptides), each of UGP021 (SEQ ID NO:4), UGP022 (SEQ ID NO:5) and UGP024 (SEQ ID NO:6) could activate both FPR1 and FPR2 by leading to ERK phosphorylation and intracellular calcium fluxes. Both UGP021 (SEQ ID NO:4) and UGP022 (SEQ ID NO:5) were observed to possess binding affinity to the FPR2 in the nanomolar range, with UGP022 (SEQ ID NO:5) showing the highest affinity. All three peptides were also observed to possess anti-inflammatory activities in an in vivo assay of leukocyte recruitment with UGP022 (SEQ ID NO:5) being, again, the more potent at inhibiting leukocyte recruitment into the inflamed air-pouch.

UGP022 (SEQ ID NO:5) exerted anti-inflammatory properties on human PMN with significance down to 1 pM. FPR2 was observed to mediate these effects of UGP022 (SEQ ID NO:5) on human PMN. In vivo, UGP022 (SEQ ID NO:5) elicited potent anti-inflammatory properties in the inflamed microcirculation with a potency equivalent to human recombinant Annexin A1. These effects were mediated by the murine orthologue of FPR2. UGP022 (SEQ ID NO:5) exhibits potent tissue protective properties in a mouse model of acute myocardial injury.

UGP025 (SEQ ID NO:7) and UGP026 (SEQ ID NO:8) retain a higher affinity to FPR2 over FPR1. UGP25 (SEQ ID NO:7) seems to have a higher affinity to FPR2 than does UGP026 (SEQ ID NO:8). UGP025 (SEQ ID NO:7) and UGP026 (SEQ ID NO:8) possess anti-inflammatory properties both in vitro and in vivo with, again, UGP025 (SEQ ID NO:7) seeming more potent. A novel property for these peptides was discovered, that is the pro-resolving effect on efferocytosis (phagocytosis of apoptotic cells). Such a pro-resolving effect of UGP022 (SEQ ID NO:5), UGP025 (SEQ ID NO:7) and UGP026 (SEQ ID NO:8) occurs in an Fpr2 dependent manner. In line with the brief biological profiling of UGP025 (SEQ ID NO:7) and UGP026 (SEQ ID NO:8), both peptides can retain the tissue protective properties of UGP022 (SEQ ID NO:5), affording cardioprotection.

Figure 6:
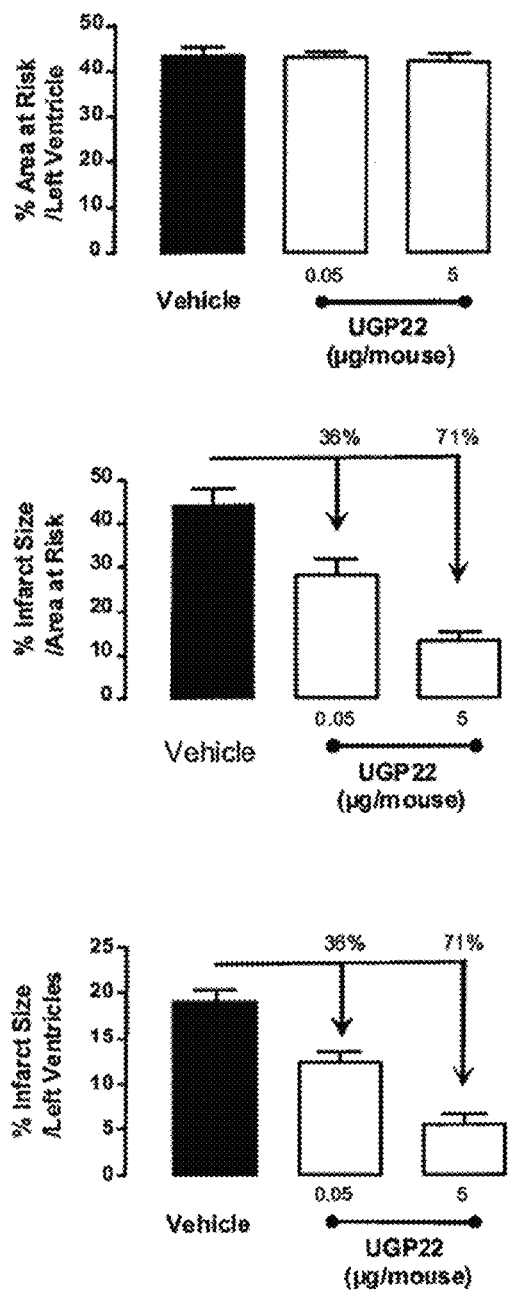
FIG. 6 is a series of bar charts showing the ability of a polypeptide UGP022 (SEQ ID NO:5)) of the present disclosure, at different concentrations, to reduce the risk of reperfusion injury relative to a vehicle-only control.
Figure 7:
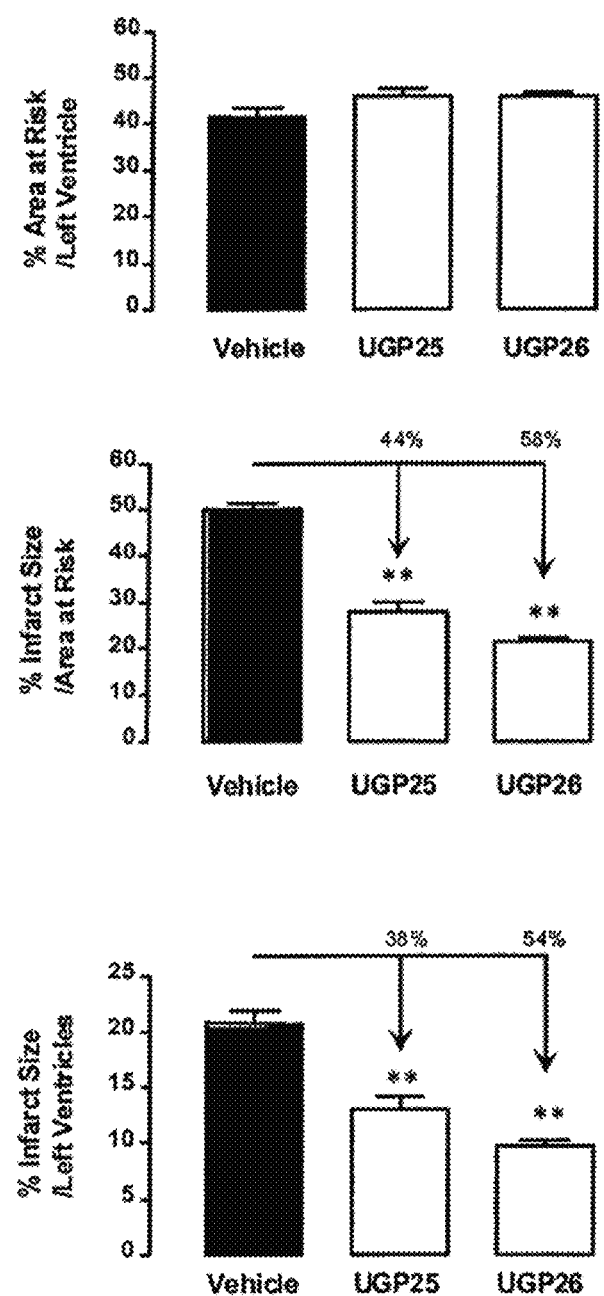
FIG. 7 is a series of bar charts showing the ability of two polypeptides (UGP025 (SEQ ID NO:7) and UGP026 (SEQ ID NO:8)) of the present disclosure, at different concentrations, to reduce the risk of reperfusion injury relative to a vehicle-only control.
Figure 8:
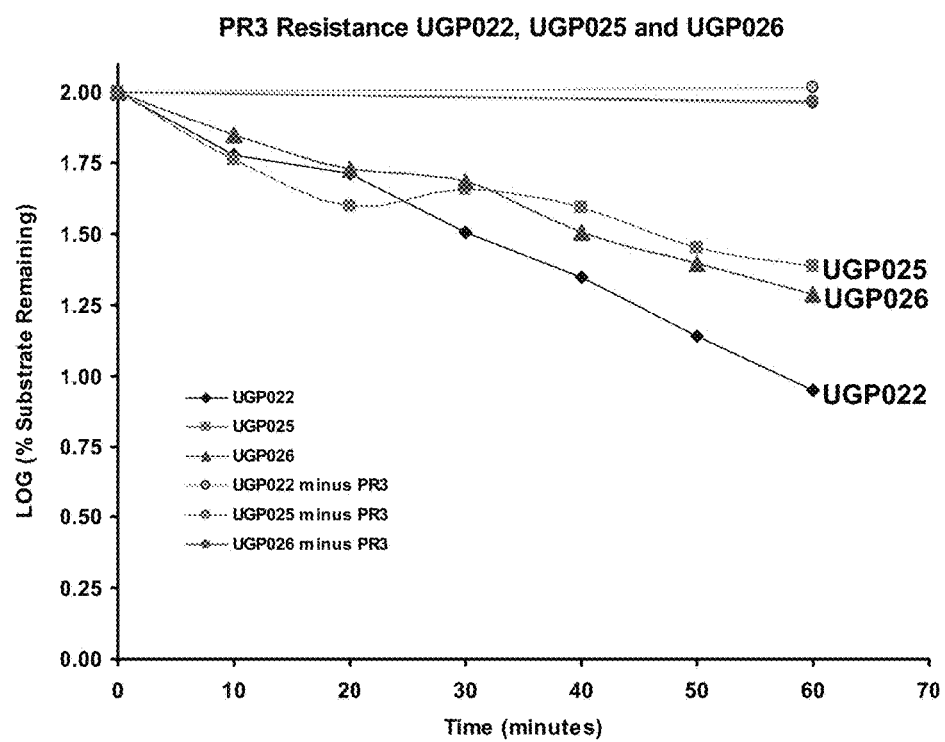
FIG. 8 is a logarithmic plot of the degradation over time of three polypeptides of the present disclosure, UGP022 (SEQ ID NO: 5), UGP025 (SEQ ID NO: 7) and UGP026 (SEQ ID NO: 8) in the presence of PR3, a protease implicated in the in vivo cleavage of Annexin 1.

FIG. 6 is a series of bar charts showing the ability of a polypeptide (UGP022 (SEQ ID NO:5)) of the present disclosure, at different concentrations, to reduce the risk of reperfusion injury relative to a vehicle-only control. Infarct size in C57/B16 mice (~30 g body weight) following 25 min ischemia (occlusion of the left anterior descending coronary artery; [LADCA]) and 120 min reperfusion. Vehicle or UGP022 (SEQ ID NO:5) were administered i.v. (over 5 sec bolus) at beginning of reperfusion. Area at Risk was measured following re-occlusion and injection of Evans blue dye. Infarct size was determined following NBT staining of the Area at Risk. Results are mean±SEM of 4 mice per group; $P<0.01$ FIG. 7 is a series of bar charts showing the ability of two polypeptides (UGP025 (SEQ ID NO:7) and UGP026 (SEQ ID NO:8)) of the present disclosure, at different concentrations, to reduce the risk of reperfusion injury relative to a vehicle-only control. Infarct size in C57/B16 mice (~30 g body weight) following 25 min ischemia (LADCA occlusion) and 120 min reperfusion. Vehicle, UGP025 (SEQ ID NO:7) (5 μg) or UGP026 (SEQ ID NO:8) (5 μg) were administered i.v. (over 5 sec bolus) at beginning of reperfusion. Area at Risk was measured following re-occlusion and injection of Evans blue dye. Infarct size was determined following NBT staining of the Area at Risk. Results are mean±SEM of 4 mice per group; $P<0.01$ FIG. 8 is a logarithmic plot of the degradation over time of three polypeptides of the present disclosure, UGP022 (SEQ ID NO:5), UGP025 (SEQ ID NO:7) and UGP026 (SEQ ID NO:8) in the presence of PR3, a protease implicated in the in vivo cleavage of Annexin 1. Better stability was observed for polypeptides with Leucine substitution at position 24 (corresponding to position 25 of Annexin 1 because all tested polypeptides lack the methionine at position 1 of natural Annexin) relative to a polypeptide lacking that feature. Also, a 47-residue polypeptide amidated at its C-terminus outperformed an otherwise identical 49-residue polypeptide amidated at its C-terminus.

Figure 9:
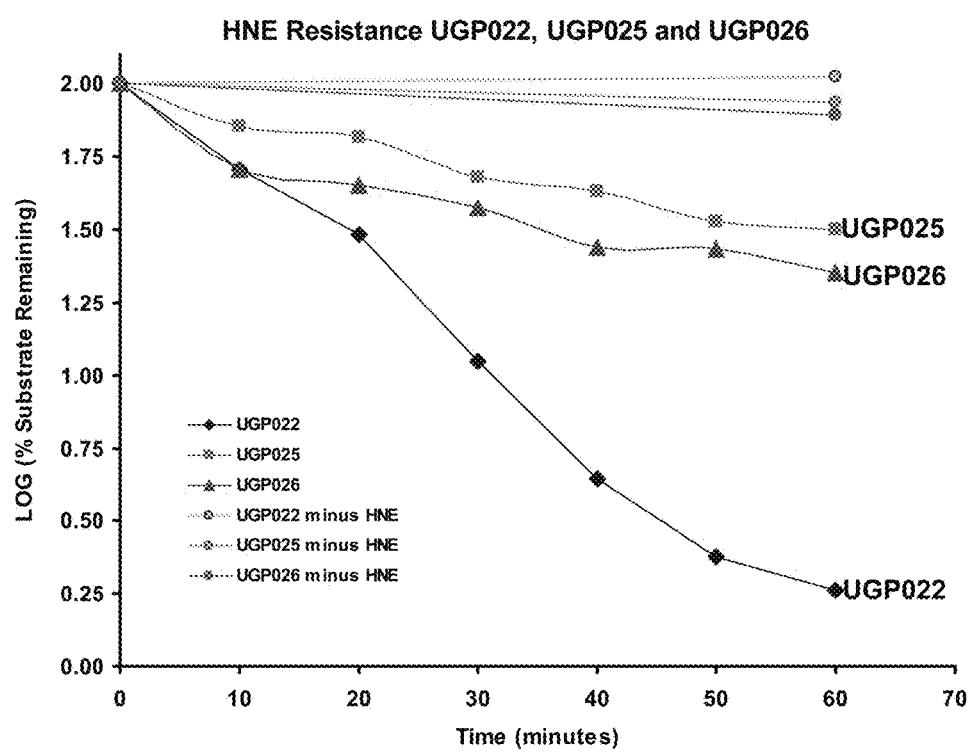
FIG. 9 is a logarithmic plot of the degradation over time of three polypeptides of the present disclosure, UGP022 (SEQ ID NO: 5), UGP025 (SEQ ID NO: 7) and UGP026 (SEQ ID NO: 8) in the presence of HNE, a protease implicated in the in vivo cleavage of Annexin 1.

FIG. 9 is a logarithmic plot of the degradation over time of three polypeptides of the present disclosure, UGP022 (SEQ ID NO:5), UGP025 (SEQ ID NO:7) and UGP026 (SEQ ID NO:8) in the presence of FINE, a protease implicated in the in vivo cleavage of Annexin 1. Better stability was observed for polypeptides with Leucine substitution at position 24 (corresponding to position 25 of Annexin 1 because all tested polypeptides lack the methionine at position 1 of natural Annexin) relative to a polypeptide lacking that feature. Also, a 47-residue polypeptide amidated at its C-terminus outperformed an otherwise identical 49-residue polypeptide amidated at its C-terminus.

Recombinant production of peptides of the present disclosure is believed to be more cost effective than other techniques known in the art, although these other techniques may also be used. Preferably, the peptides of the present disclosure are amidated at their C-terminus, although free acid forms are also contemplated. A technique for manufacturing amidated versions of the peptides of the present disclosure is to react precursors (having glycine in place of the C-terminal amino group of the desired amidated product) in the presence of peptidylglycine alpha-amidating monooxygenase in accordance with known techniques wherein the precursors are converted to amidated products in reactions described, for example, in U.S. Pat. No. 4,708, 934 and European Patent Publication Nos. 0 308 067 and 0 382 403. Recombinant production is preferred for both the precursor and the enzyme that catalyzes the conversion of the precursor to salmon calcitonin. Such recombinant production is discussed in Biotechnology, Vol. 11 (1993) pp. 64-70, which further describes a conversion of a precursor to an amidated product. Production of amidated products may also be accomplished using the process and amidating enzyme set forth by Consalvo et al. in U.S. Pat. No. 7,445,911; Miller et al. in U.S. Patent Publication No. 2006/0292672; Ray et al, 2002, Protein Expression and Purification, 26:249-259 ("Ray"); and Mehta, 2004, Biopharm. International, July, pp. 44-46 ("Mehta").

The production of the amidated peptides of the present disclosure may proceed, for example, by producing glycine-extended precursor in E. coli as a soluble fusion protein with glutathione-S-transferase, or by direct expression of the precursor in accordance with the technique described in U.S. Pat. No. 6,103,495. Such a glycine extended precursor has a molecular structure that is identical to the desired amidated product except at the C-terminus (where the product terminates —X—NH$_2$, while the precursor terminates —X-gly, X being the C-terminal amino acid residue of the product). An alpha-amidating enzyme described in the publications above catalyzes conversion of precursors to product. That enzyme is preferably recombinantly produced, for example, in Chinese Hamster Ovary (CHO) cells), as described in the Biotechnology and Biopharm. articles cited above.

Free acid forms of peptide active agents of the present disclosure may be produced in like manner, except without including a C-terminal glycine on the "precursor", which precursor is instead the final peptide product and does not require the amidation step.

The description below provides an embodiment of a method of cloning and expression of ANXA1 peptides and analogues of the present disclosure. ANXA1 peptides and analogues of the present disclosure were designed for cloning and expression using vectors for extracellular expression in E. coli. The designed genes were synthesized by DNA 2.0 (Menlo Park, Calif.) using their codon optimization algorithm, followed by single amino acid modifications using PCR in the noted constructs. The vector design for these constructs was based on the vector presented in Ray, such that the gene of interest is encoded in dual cassettes with each cassette comprised of dual promoters and a signal sequence preceding the gene of interest, and dual transcription termination sequences following the gene of interest.

| Gene | Source | Gene Modification |
|---|---|---|
| ANXA1(2-50)-OH | DNA 2.0 | NA |
| ANXA1(2-50)Gly51-OH | DNA 2.0 | NA |
| ANXA1(2-48)Gly49-OH | DNA 2.0 | optimized amino acid codons of ANXA1(2-50)Gly51-OH |
| Leu25-ANXA1(2-48)Gly49 | ANXA1 (2-50) gene template | PCR, Val to Leu @ 25 incorporated into PCR primer |
| Leu25-ANXA1(2-50)Gly51-OH | ANXA1 (2-50) gene template | PCR, Val to Leu @ 25 incorporated into PCR primer |

The digenic plasmid construct of each analog was used to transform Applicants proprietary E. coli host strain, BLM6L, having Accession Number PTA-5500, resulting in expression strains for each analog gene construct. These recombinant cell lines were screened for kanamycin resistance and growth at 37° C. in a semi-defined inoculation media, as described in Ray; the plasmid constructs were confirmed with diagnostic restriction enzyme mapping, and final isolates were screened in shake flask experiments for the extracellular production of the peptide of interest, using a AEX-HPLC assay, described elsewhere. Selected isolates were further evaluated in bench scale fermentations. Each fermentation was run as a substrate limited, fed batch run with the induction of recombinant protein achieved using the chemical inducer, IPTG, which was incorporated into the feed. The fermentation was run under standard conditions of 32° C., pH 6.6, and dissolved oxygen at 80% by supplementation with O$_2$ in media as described in Ray. These fermentations were assayed and in some cases harvested between 23 and 31 hours post induction. For purification the fermentation was acidified and chilled; the conditioned media was harvested by centrifugation for downstream processing.

| ANXA1 Peptide | Cell Line Designation | Fermentation Titer (mg/L)* |
|---|---|---|
| ANXA1(2-50)-OH | UGL945 | 110 |
| ANXA1(2-50)Gly51-OH | UGL946 | 202 |
| ANXA1(2-48)Gly49-OH | UGL962 | 110 |
| Leu25-ANXA1(2-48)Gly49-OH | UGL977 | 91 |
| Leu25-ANXA1(2-50)Gly51-OH | UGL978 | 121 |

*Fermentation productivity values were determined by AEX-HPLC.

In an embodiment of the present disclosure, recombinant peptides were purified from 1 L of conditioned fermentation medium. Each peptide was precipitated from the conditioned medium by acidification to approximately pH 2 with 2 N H$_2$SO$_4$. Pellets were collected by centrifugation for 1 hour at 10,000 rpm. Pellets were re-suspended in 25 mM NaH2PO4 pH 7.8 overnight at 2-8° C. Re-suspensions were centrifuged for 30 minutes at 10,000 rpm. The supernatant pH was adjusted to 8.5 with 2 N NaOH. Each pH adjusted supernatant was loaded onto a Q-Sepharose Big Beads (GE Healthcare) anion exchange column (4.4×13.5 cm) equilibrated with 25 mM TRIS pH 8.5. The column was operated at a flow rate of 30 mL/min. and the UV absorbance of column effluent was monitored 280 nm. ANXA1 peptides were eluted from the column with 25 mM TRIS, 100 mM NaCl pH 8.5. Collected fractions were screened by AEX-HPLC and RP-HPLC.

C-terminal α-amidation (if required) was carried out using recombinant peptidylglycine alpha-amidating monooxygenase (rPAM). α-Amidation of glycine-extended ANXA1 peptides were carried out at 0.5 mg/mL in the presence of 25 mM TRIS pH 7.0 (JT Baker), 0.5 µM CuSO$_4$ (JT Baker), 1% ethanol, 125 U/mL aspergius niger catalase (BBI Enzymes), 3 mM ascorbate and 20,000 U/mL rPAM. Reactions were incubated at 37° C. for 2-3 hours. Reactions were terminated by flash freezing.

α-Amidation outputs were loaded onto an Amberchrom CG300 (Dow Chemical) RP column (1.1×13.7 cm) equilibrated with 0.1% TFA, 2% MeCN. The column was operated at a flow rate of 2.85 mL/min. and the UV absorbance of column effluent was monitored 280 nm. The column was subjected to a step-gradient with 0.1% TFA, 16% MeCN and 0.1% TFA, 24% MeCN to remove impurities. ANXA1 peptides were eluted from the column with 0.1% TFA, 40% MeCN. Collected fractions were screened by AEX-HPLC and RP-HPLC.

ANXA1 peptides were lyophilized to dryness using a VirTis Freeze Mobile Consol 1.5 (Gardiner, N.Y.) fitted with a vacuum controller and external dry-ice/acetone condenser. The final purity of the ANXA1 peptides were >95% assessed by AEX/RP-HPLC.

Purity and fermentation productivity (titer) of the ANAX1 peptides were determined by AEX-HPLC. Chromatography was carried out on a Hydrocell QA1500 column (BioChrom Labs), 4.6×250 mm equilibrated with 10 mM TRIS, 25% MeCN pH 8.0. Separation was achieved using a linear gradient from 0% A (10 mM TRIS, 25% MeCN pH 8.0) to 20% B (10 mM TRIS, 0.5 M NaCl, 25% MeCN pH 8.0) over 20 minutes. The column was operated at ambient temperature at a flow rate of 1.2 mL/min. The UV absorbance of the column effluent was monitored at 220 nm. Productivity values were determined based on standard curve for each peptide.

Purity of the ANAX1 peptides was determined by RP-HPLC. Chromatography was carried out on a Thermo Electron BDS Hypersil C18 column (Thermo Fisher Scientific), 4.6×250 mm, 5 µm, 120 Å equilibrated with 0.1% TFA, 18% MeCN. Separation was achieved using a linear gradient from 20% B to 70% B (mobile phase A: 0.1% TFA; mobile phase B: 0.08% TFA, 90% MeCN) over 20 minutes. The column was operated at ambient temperature at a flow rate of 1.2 mL/min. The UV absorbance of the column effluent was monitored at 220 nm.

It is estimated that peptides of the present disclosure should be administered at adequate dosage to maintain serum levels of the peptide in patients between 0.1 and 100 nanograms per milliliter, preferably between 5 and 50 nanograms per milliliter. The serum levels may be measured by radioimmunoassay techniques known in the art. The attending physician may monitor patient response, and may then alter the dosage somewhat to account for individual patient metabolism and response.

The compounds used in the present disclosure are preferably prepared for use as pharmaceuticals. The polypeptides may be administered by any suitable route commonly used in the pharmaceutical industry, including but not limited to oral, parenteral, intramuscular, transdermal or transmucosal delivery. IV infusions may also be utilized in some embodiments. Ocular drops may be used in eye treatments. In some embodiments, the polypeptides may be administered in conjunction with other anti-inflammatory agents.

While other delivery methods may be used, a peptide of the present disclosure may be formulated for oral delivery, for example as set forth in U.S. Pat. No. 6,086,018, or U.S. Patent Publication No. 2009/0317462. One oral dosage form in accordance with the present disclosure is set forth (by way of example and not of limitation) in Table 1 below:

TABLE 1

| COMPONENTS OF SOLID DOSAGE FORMULATION | |
|---|---|
| ACTIVE AGENT OR EXCIPIENT | FUNCTION |
| UGP025 (the polypeptide of SEQ ID NO: 7) | Active agent for suppression of inflammation |
| Glucose Polymer (Maltodextrin) Coated Citric Acid particles | Protease Inhibitor |
| Lauroylcarnitine | Absorption Enhancer |
| Nonionic Polymer | Subcoat |
| Eudragit L30D-55 | Enteric Coat |

While the peptide of SEQ ID NO: 7 is given as an example, any peptide active agent, discussed herein may be substituted as the active agent. A combination of two or more such agents may also be substituted.

A tablet of the present disclosure comprises a polypeptide of the present disclosure and at least one pharmaceutically acceptable acid wherein acid is present in the tablet in a quantity which, if the tablet were added to 10 milliliters of 0.1M aqueous sodium bicarbonate solution, would be sufficient to lower the pH of the solution to no higher than 5.5. Preferably the acid comprises acid particles that are coated with a pharmaceutically acceptable protective coating that is non-acidic and has a solubility in water of at least one gram per 100 milliliters of water at room temperature. In some embodiments, the outer surface of the tablet is an acid resistant protective vehicle effective to transport the tablet through the stomach of a patient while preventing contact between the active polypeptide and stomach proteases (e.g. a common pharmaceutical enteric coating). It is preferred that such tablet have a water soluble barrier layer that separates the coated acid from the protective vehicle. Where present, the water-soluble barrier layer either (a) adds at least 3% to the weight of the pharmaceutical composition, exclusive of any acid-protective vehicle, and/or (b) comprises a material having water solubility in excess of 11 grams per 100 milliliters of water at room temperature. Preferably, the peptide agent and the acid are in the same or only layer of the composition. Prior experience with oral delivery of prior art peptides suggest that oral delivery as described herein might provide as much as 1-5 percent bioavailability.

Administration may be by either a single daily dosage or multiple dosages. Regardless of the active agent being administered, it is preferred that a single dosage form (for example, a single capsule or tablet when oral administration is utilized) be used at each administration because a single capsule or tablet best provides simultaneous release of the peptide active agent, acid (used as protease inhibitor) and absorption enhancers. This is highly desirable because the acid is best able to reduce undesirable proteolytic attack on the peptide active agent when the acid is released in close time proximity to release of the active agent.

Near simultaneous release is best achieved by administering all components of the disclosure as a single pill or capsule. However, the disclosure also includes, for example, dividing the required amount of the active ingredient among two or more tablets or capsules which may be administered together such that they together provide the necessary amount of all ingredients. "Pharmaceutical composition," as used herein includes but is not limited to a complete dosage appropriate to a particular administration to a patient regardless of whether one or more tablets or capsules (or other dosage forms) are recommended at a given administration.

Peptides in accordance with the present disclosure may also be delivered by other common techniques in the industry with normal dosage variations between modes of administration. For example, a dosage range between 1 and 100 micrograms per day, (preferably between 5 and 50 micrograms per day, is believed likely to be adequate when administered by injection. Naturally, the attending clinician should monitor individual patient response and adjust dosage accordingly.

In a pharmaceutical composition for injection, the peptide active agent of the present disclosure is preferably present in a concentration between 10 micrograms/milliliter and 1000 micrograms per milliliter.

Pharmaceutical compositions of the present disclosure may include typical pharmaceutical excipients, diluents or carriers, such as water, saline, glycerol, ethanol, etc. Additionally or alternatively, auxiliary substances, such as wetting or emulsifying agents, pH buffering substances, and the like, may be present in such vehicles. Other non-limiting examples of excipients include but is not limited to pharmaceutically acceptable excipients such as 0.1 M PBS (pH 7.4), 0.2 M NaHCO$_3$ or other such pharmaceutically acceptable fluids. The compositions may be prepared as injectables, either as liquid solutions or suspensions. Solid forms suitable for solution in, or suspension in, liquid vehicles prior to injection may also be prepared. The preparation also may be emulsified or encapsulated in, for example, liposomes.

Compositions used as pharmaceuticals comprise an effective amount of the compound, as well as any other of the above-mentioned components, as needed. By "effective amount", it is meant that the administration of that amount to an individual, either in a single dose or as part of a series, is effective for treatment or prevention of inflammation. This amount varies depending upon the health, age and physical condition of the individual to be treated, the taxonomic group of individual to be treated (e.g., non-human primate, primate, etc.), and other common factors affecting the attending clinician's assessment of the dosage requirements.

In an embodiment, a polypeptide of the present disclosure has 47-50 amino acids and including within its molecular structure a region of homology that has at least 90 percent identity to residues 2-48 of SEQ ID NO: 1, wherein residue 24 of the polypeptide corresponds to residue 25 of SEQ ID NO: 1, and wherein residue 24 of the polypeptide is not valine.

In an embodiment, a polypeptide of the present disclosure has 25-26 amino acids and including within its molecular structure a region of homology that has at least 90 percent identity to residues 2-26 of SEQ ID NO: 1, wherein residue 10 of the polypeptide corresponds to residue 11 of SEQ ID NO: 1, wherein residue 10 of the polypeptide is any amino acid except for alanine, and wherein residue 21 of the peptide is any amino acid except for valine.

In an embodiment, a polypeptide of the present disclosure has 37-45 amino acids and including within its molecular structure a region of homology that is 100 percent identical to residues 12-24 of SEQ ID NO: 1 and 100 percent identical to residues 26-48 of SEQ ID NO:1, wherein either residue 14 of the polypeptide corresponds to residue 25 of SEQ ID NO: 1 and is not valine, or wherein residue 21 of the polypeptide corresponds to residue 25 of SEQ ID NO: 1 and is not valine.

In an embodiment, a polypeptide of the present disclosure has 47-50 amino acids and including within its molecular structure a region of homology that is 100 percent identical to residues 2-48 of SEQ ID NO: 1, wherein the polypeptide is amidated at its C-terminus.

In an embodiment, a polypeptide of the present disclosure has from 37 to 51 amino acid residues and includes within its molecular structure a region of homology that is at least 90 percent identical to SEQ ID NO: 2, wherein the homology region of the polypeptide has at least one of the following characteristics: (a) residue 10 of the polypeptide corresponding to residue 1 of SEQ ID NO: 2 is not alanine, (b) residue 21 of the polypeptide corresponding to residue 12 of SEQ ID NO: 2 is not valine, (c) residue 24 of the polypeptide corresponding to residue 15 of SEQ ID NO: 2 is not valine or (d) residue 35 of the polypeptide corresponding to residue 26 of SEQ ID NO: 2 is not valine. In an embodiment, the homology region of the polypeptide has at least two of the following characteristics: (a) residue 10 of the polypeptide corresponding to residue 1 of SEQ ID NO: 2 is not alanine, (b) residue 21 of the polypeptide corresponding to residue 12 of SEQ ID NO: 2 is not valine, (c) residue 24 of the polypeptide corresponding to residue 15 of SEQ ID NO: 2 is not valine or (d) residue 35 of the polypeptide corresponding to residue 26 of SEQ ID NO: 2 is not valine. In an embodiment, the homology region of the polypeptide has at least three of the following characteristics: (a) residue 10 of the polypeptide corresponding to residue 1 of SEQ ID NO: 2 is not alanine, (b) residue 21 of the polypeptide corresponding to residue 12 of SEQ ID NO: 2 is not valine, (c) residue 24 of the polypeptide corresponding to residue 15 of SEQ ID NO: 2 is not valine or (d) residue 35 of the polypeptide corresponding to residue 26 of SEQ ID NO: 2 is not valine. In an embodiment, the homology region of the polypeptide has each of the following characteristics: (a) residue 10 of the polypeptide corresponding to residue 1 of SEQ ID NO: 2 is not alanine, (b) residue 21 of the polypeptide corresponding to residue 12 of SEQ ID NO: 2 is not valine, (c) residue 24 of the polypeptide corresponding to residue 15 of SEQ ID NO: 2 is not valine and (d) residue 35 of the polypeptide corresponding to residue 26 of SEQ ID NO: 2 is not valine. In an embodiment, residue 24 of the polypeptide corresponding to residue 15 of SEQ ID NO: 2 is not valine. In an embodiment, residue 24 of the polypeptide corresponding to residue 15 of SEQ ID NO: 2 is leucine. In an embodiment, the homology region of the polypeptide is at least 94 percent identical to SEQ ID NO: 2. In an embodiment, the homology region of the polypeptide is 100 percent identical to SEQ ID NO: 2. In an embodiment, the polypeptide is amidated at its C-terminus.

In an embodiment, a polypeptide of the present disclosure has 47 to 48 amino acids and has at least 90 percent identity to residues 1-48 of SEQ ID NO: 1. In an embodiment, the polypeptide has at least one of the following characteristics: (a) residue 10 of the polypeptide corresponding to residue 11 of SEQ ID NO: 1 is not alanine, (b) residue 21 of the polypeptide corresponding to residue 22 of SEQ ID NO: 1 is not valine, (c) residue 24 of the polypeptide corresponding to residue 25 of SEQ ID NO: 1 is not valine or (d) residue 35 of the polypeptide corresponding to residue 36 of SEQ ID NO: 1 is not valine.

In an embodiment, a polypeptide of the present disclosure has at least 96 percent identity to SEQ ID NO: 11, wherein either residue 10 is not alanine or residue 21 is not valine. In an embodiment, residues 10 and 21 of the polypeptide are independently selected from aspartic acid, lysine, methionine, leucine, isoleucine and glutamic acid. In an embodiment, residues 10 and 21 of the polypeptide are independently selected from leucine, aspartic acid, methionine, isoleucine and glutamic acid. In an embodiment, residues 10 and 21 of the polypeptide are independently selected from the group consisting of leucine, aspartic acid and methionine. In an embodiment, the polypeptide has identical amino acids at positions 10 and 21. In an embodiment, residue 1 of the polypeptide is acetylated.

In an embodiment, a polypeptide of the present disclosure has an amino acid sequence as set forth in SEQ ID NO: 11, wherein either residue 10 is not alanine or residue 21 is not valine. In an embodiment, residues 10 and 21 of the polypeptide are independently selected from aspartic acid, lysine, methionine, leucine, isoleucine and glutamic acid. In an embodiment, residues 10 and 21 of the polypeptide are independently selected from leucine, aspartic acid, methionine, isoleucine and glutamic acid. In an embodiment, residues 10 and 21 of the polypeptide are independently selected from leucine, aspartic acid and methionine. In an embodiment, the peptide has identical amino acids at positions 10 and 21. In an embodiment, the polypeptide is amidated at its C-terminus.

In an embodiment, a polypeptide of the present disclosure has from 47 to 51 amino acid residues and includes within its molecular structure a region of 47 amino acid residues that is 100 percent identical to residues 2-48 of human Annexin 1. In an embodiment, the polypeptide has from 49-51 amino acid residues. In an embodiment, the polypeptide is amidated at its C-terminus.

In an embodiment, a pharmaceutical composition of the present disclosure includes a polypeptide of the present disclosure. In an embodiment, the pharmaceutical composition is in the form of a tablet or capsule. In an embodiment, the tablet or capsule comprises at least one pharmaceutically acceptable acid. In an embodiment, the acid is present in the tablet or capsule in a quantity which, if the tablet or capsule, were added to 10 milliliters of 0.1M aqueous sodium bicarbonate solution, would be sufficient to lower the pH of the solution to no higher than 5.5. In an embodiment, the acid comprises acid particles that are coated with a pharmaceutically acceptable protective coating. In an embodiment, the protective coating is non-acidic. In an embodiment, the protective coating has a solubility in water of at least one gram per 100 milliliters of water at room temperature. In an embodiment, an outer surface of a tablet or capsule of the present disclosure is an acid resistant protective vehicle effective to transport the tablet or the capsule through the stomach of a patient while preventing contact between the active polypeptide and stomach proteases. In an embodiment, a tablet or capsule of the present disclosure includes a water soluble barrier layer that separates coated acid in the tablet or capsule from the protective vehicle, wherein the water-soluble barrier layer either (i) adds at least 3% to the weight of the pharmaceutical composition, exclusive of any acid-protective vehicle, or (ii) comprises a material having water solubility in excess of 11 grams per 100 milliliters of water at room temperature.

All patents, patent applications, and published references cited herein are hereby incorporated by reference in their entirety. It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method of treating inflammation comprising administering to a patient in need of such treatment a therapeutically effective amount of an isolated polypeptide selected from the group consisting of the amino acid sequence consisting of SEQ ID NO: 5 and the amino acid sequence consisting of SEQ ID NO: 6.

2. A method of treating inflammation comprising administering to a patient in need of such treatment a therapeutically effective amount of a pharmaceutical composition comprising an isolated polypeptide selected from the group consisting of the amino acid sequence consisting of SEQ ID NO: 5 and the amino acid sequence consisting of SEQ ID NO: 6.

3. The method of claim 1, wherein residue 1 of the isolated polypeptide is acetylated.

4. The method of claim 1, wherein the method comprises treating inflammation of the eye, gout, gouty arthritis, asthma, reperfusion injury or damage, stroke, myocardial infarction, septic shock, or an inflammatory skin disorder.

5. The method of claim 2, wherein the pharmaceutical composition further comprises one or more pharmaceutically acceptable excipient, diluent, or carrier.

6. The method of claim 4, wherein the inflammatory skin disorder is psoriasis or eczema.

* * * * *